(12) United States Patent
Corneliusson

(10) Patent No.: US 7,918,840 B2
(45) Date of Patent: Apr. 5, 2011

(54) ABSORBENT ARTICLE

(75) Inventor: Helena Corneliusson, Bohus (SE)

(73) Assignee: SCA Hygiene Products AB, Gothenburg (SE)

( * ) Notice: Subject to any disclaimer, the term of this patent is extended or adjusted under 35 U.S.C. 154(b) by 394 days.

(21) Appl. No.: 10/790,793

(22) Filed: Mar. 3, 2004

(65) Prior Publication Data

US 2004/0181202 A1 Sep. 16, 2004

Related U.S. Application Data

(60) Provisional application No. 60/454,344, filed on Mar. 14, 2003.

(51) Int. Cl.
*A61F 13/15* (2006.01)

(52) U.S. Cl. ......... 604/385.28; 604/385.22; 604/385.24; 604/385.25; 604/385.26; 604/385.27; 604/385.29

(58) Field of Classification Search .. 604/385.24–385.3, 604/385.1, 385.2, 385.01, 385.101, 385.22
See application file for complete search history.

(56) References Cited

U.S. PATENT DOCUMENTS

| | | | | |
|---|---|---|---|---|
| 4,695,278 A | * | 9/1987 | Lawson | 604/385.27 |
| 5,026,364 A | * | 6/1991 | Robertson | 604/385.3 |
| 5,114,420 A | * | 5/1992 | Igaue et al. | 604/385.26 |
| 5,397,318 A | * | 3/1995 | Dreier | 604/385.19 |
| 5,407,438 A | * | 4/1995 | Hedlund et al. | 604/385.26 |
| 5,496,428 A | * | 3/1996 | Sageser et al. | 156/73.1 |
| 5,577,540 A | * | 11/1996 | Sageser | 156/226 |
| 5,593,401 A | | 1/1997 | Sosalla et al. | |
| 5,634,916 A | * | 6/1997 | Lavon et al. | 604/385.22 |
| 5,695,488 A | | 12/1997 | Sosalla | |
| 5,746,732 A | * | 5/1998 | Olsson et al. | 604/385.28 |
| 5,752,947 A | | 5/1998 | Awolin | |
| 6,142,985 A | | 11/2000 | Feist | |
| 6,312,420 B1 | | 11/2001 | Sasaki et al. | |

FOREIGN PATENT DOCUMENTS

| | | |
|---|---|---|
| EP | 0 740 929 | 11/1996 |
| EP | 0 951 890 A2 | 10/1999 |
| EP | 1 232 736 A1 | 8/2002 |
| EP | 1 273 281 A2 | 1/2003 |

(Continued)

OTHER PUBLICATIONS

Translation of JP 64-77607.*

(Continued)

*Primary Examiner* — Jacqueline F Stephens
(74) *Attorney, Agent, or Firm* — Buchanan Ingersoll & Rooney PC

(57) ABSTRACT

An absorbent article includes an upper, liquid-permeable cover sheet, a lower, liquid-impermeable cover sheet, and an absorption body arranged between the cover sheets. The article includes first and second side barriers along the respective longitudinal sides of the article. Each side barrier has at least one longitudinal elastic element. The side barriers define a shape which narrows in the direction towards the front portion so that the distance, in the transverse direction of the article, between the elastic elements is greater in the rear portion than in the front portion. Each side barrier is arranged such that, when it is secured in contact with the front portion, each side barrier and the upper cover sheet define a folded structure of substantially Z-shaped cross section with a fold directed towards the inside of the article.

19 Claims, 3 Drawing Sheets

FOREIGN PATENT DOCUMENTS

| | | |
|---|---|---|
| ES | 2132410 | 3/1996 |
| ES | 2149399 | 11/1996 |
| ES | 2183880 | 4/2003 |
| JP | 6426310 U * | 2/1982 |
| JP | 6477607 A * | 3/1989 |
| JP | 1-298202 A | 12/1989 |
| JP | 422359 A * | 1/1992 |
| JP | 2001-137282 | 5/2001 |
| WO | WO 94/28840 | 12/1994 |
| WO | WO 96/03951 | 2/1996 |
| WO | 02/49560 A1 | 6/2002 |

OTHER PUBLICATIONS

Definition of "tack", Webster's Third New International Dictionary, Unabridged.*

Definition of "tack", Merriam-Webster OnLine.*

Columbian Official Action dated May 14, 2009 issued in corresponding application No. 05092061.

English Translation of Japanese Office Action issued in Japanese Application No. 2006-507954 dated Jul. 21, 2009.

English Translation of Columbian Office Action issued in corresponding Application No. 05092061.

* cited by examiner

ABSORBENT ARTICLE

CROSS-REFERENCE TO RELATED APPLICATIONS

The present application claims the benefit of U.S. Provisional Application No. 60/454,344, filed in the United States on Mar. 14, 2003, the entire contents of which are hereby incorporated herein by reference.

BACKGROUND OF THE APPLICATION

1. Technical Field

The present invention relates to an absorbent article comprising an upper, liquid-permeable cover sheet, a lower, liquid-impermeable cover sheet, and an absorption body arranged between the cover sheets.

2. Background Art

In connection with absorbent articles such as diapers, incontinence protectors for adults, and sanitary towels, there has long been a general need for materials and structures which are able to take up, distribute and absorb bodily excretions in a rapid and effective manner. Today's absorbent articles generally have good absorbency with a low risk of leakage and a high degree of comfort for the person wearing the absorbent article.

The requirement for rapid and effective absorbency is important not least in the case of diapers for very small infants and also for premature babies (i.e. babies born before pregnancy has reached its full term). In this connection, it should be noted that infants and premature babies produce excrement which is loose and runny in consistency. With today's diapers for infants, there is a risk of this loose excrement leaking at the sides in the crotch area and out towards the user's legs, and also along the back of the person wearing the diaper. Such leakage may entail a risk of, for example, soiling of clothes and bed linen. In general, it may be stated that, in connection with diapers for infants, ever greater demands are being placed on the ability to take up excreted material.

According to the prior art, a diaper for infants is normally made up of an upper, liquid-permeable cover sheet and a lower, liquid-impermeable cover sheet. An absorption body is arranged between these cover sheets. To prevent urine and excrement leaking out at the sides, i.e. in the transverse direction of the diaper, the latter is normally provided with two side barriers which extend in the longitudinal direction of the diaper, along each side. Moreover, these side barriers are designed so that they are raised slightly from the surface of the diaper. The side barriers can be provided with longitudinal elastic elements, such as threads or bands, in order to give the barriers their desired shape. In addition to having these longitudinal barriers, today's diapers are normally also provided with further longitudinal elements along the side edges, more specifically in the area at the user's crotch. These further longitudinal elements are also made with elastic elements and constitute so-called leg elastic which is intended to ensure that the diaper fits well and provides a seal against the user's legs.

With regard to diapers intended to be used on very small infants or premature babies (who may have a bodyweight of the order of 1 kg), there is a need to abandon the abovementioned known type of diaper construction. In particular, there is a need to use diapers which as far as possible use up a small amount of material, and the material must additionally be especially soft and gentle against the child's skin. For this reason, the abovementioned structure with separate side barriers and leg elastic does not appear to be suitable for diapers intended, for example, for premature babies.

Patent document EP 951890 discloses an absorbent article in the form of a diaper which is of a type comprising two side barriers oriented along a respective side of the diaper. Each of the side barriers comprises two longitudinal elastic elements. This arrangement provides a structure in which each side barrier is raised and additionally forms two longitudinal channels to the inside of each side barrier. The risk of lateral leakage of urine and excrement is reduced in this way. It should be noted that this known diaper has a structure with only one side barrier, in contrast to the type comprising both leg elastic and separate side barriers.

Although the diaper described in EP 951890 affords a basically satisfactory function, there is a need for further improved uptake, distribution and absorption of loose excrement in the type of diapers used on very small infants and in particular in the type used on premature babies. There is a need, not least, to reduce the risk of lateral leakage of loose excrement towards the user's legs. In addition to the need for reliable protection against lateral leakage, there are also corresponding requirements to reduce a risk of excrement leaking out at the rear and up towards the user's back. Moreover, it is particularly required that the type of diaper in question provides a good fit.

OBJECTS AND SUMMARY

A principal object of the present invention is to make available an improved absorbent article in which the above requirements and needs are satisfied. It is in particular an object of the invention to make available an absorbent article in the form of a diaper, for very small infants and premature babies, which uses a structure with only one side barrier along each side and which effectively prevents leakage of urine and excrement both laterally and at the rear of the article.

The above objects are achieved with an absorbent article of the type mentioned in the introduction, which article is arranged such that the article defines a longitudinal direction, a front portion in the longitudinal direction, a rear portion, and a middle portion arranged between said front and rear portions, and comprises: an upper, liquid-permeable cover sheet, a lower, liquid-impermeable cover sheet, an absorption body arranged between the cover sheets, a rear barrier formed in the rear portion and attached to the article along the rear edge of the article, and first and second side barriers along respective longitudinal sides, each side barrier in turn comprising at least one longitudinal elastic element, said first and second side barriers, viewed from above, defining a shape which narrows in the direction towards said front portion so that the distance, in the transverse direction of the article, between said elastic elements, is greater in said rear portion than in said front portion. Each side barrier is arranged such that, when it is secured in contact with said front portion, each side barrier and the upper cover sheet define a folded structure of substantially Z-shaped cross section with a fold directed towards the inside of said article. The at least one longitudinal elastic element of each side barrier is positioned at or near the fold directed towards the inside of the article. The at least one longitudinal elastic element of each side barrier runs between an attachment point on the front portion of the article and an attachment point on the rear portion of the article and along the entire length of the fold directed towards the inside of the article. The first side barrier is secured to the cover sheet to form a first line of attachment, and the second side barrier is secured to the cover sheet to form a second line of attachment, the first and second lines of attachment extending under the rear barrier, and the first and second side barriers cooperate with the rear barrier to form a pocket, the pocket extending to the rear edge of the article and continuously between and beyond the first and second lines of attachment in respective outward transverse directions of the article.

According to one aspect, the elastic element in the first side barrier, viewed from above, is secured to the rear portion outside the first line of attachment, and the elastic element in the second side barrier, viewed from above, is secured to the rear portion outside the second line of attachment.

According to another aspect, the rear barrier is intended for taking up bodily excretions in the direction rearwards along the article.

According to another aspect, the rear barrier comprises a further elastic element.

According to another aspect, the further elastic element, when viewed from above, extends outside the attachment points on the rear portion of the article, and the further elastic element comprises attachment points which, when viewed from above, extend outside the attachment points of the elastic elements in the side barriers on the rear portion of the article, a barrier being defined along the longitudinal sides and rear side of the article.

According to another aspect, the first side barrier comprises a first elastic element and a second elastic element, the second side barrier comprises a third elastic element and a fourth elastic element, the first elastic element extending outside the second elastic element viewed in relation to a longitudinal axis of symmetry through the article, and the third elastic element extending outside the fourth elastic element viewed in relation to the axis of symmetry.

According to another aspect, the distance between the elastic elements of the side barriers is at least two times greater at the rear portion than at the front portion.

According to another aspect, the distance between the elastic elements of the side barriers is at least three times greater at the rear portion than at the front portion.

According to another aspect, the distance between parts of the elastic elements in the side barriers nearest to the inside of the article is within the range of 1-3 cm at the front portion.

According to another aspect, the elastic elements run at least partially in contact with the folds in each side barrier.

According to another aspect, the first and second side barriers by themselves constitute a combined side leakage protection and leg elastic for the article.

According to another aspect, the elastic elements consist of elastic threads.

According to another aspect, the pocket is provided beyond the absorption body in the longitudinal direction.

According to another aspect, the first and second side barriers form a side barrier of the pocket in the longitudinal direction of the article, the side barrier of the pocket being disposed beyond the first and second lines of attachment in the transverse direction of the article.

According to another aspect, the at least one longitudinal elastic element of each side barrier is positioned at or near the fold along an entire length of the at least one longitudinal elastic element.

The invention affords certain advantages. In particular, it should be noted that the invention provides the possibility of making available an absorbent article such as a diaper which is easy to place on small children, which provides a good fit and which provides good leakage protection both laterally and at the rear of the diaper. The invention also provides a combined function of lateral leakage protection and leg elastic, thereby permitting savings in terms of material and making the article light and flexible for the user. It may be noted in particular that the above-mentioned narrowing shape of the elastic elements of the side barriers, in combination with the Z-shaped folded attachment of each side barrier to the front portion of the article, means that each side barrier, during use, is raised very distinctly and effectively in relation to the surface of the diaper. In addition, a cup shape is thus formed which adapts in a reliable manner to the user's anatomy and contributes to the good fit. In addition, a diaper designed according to the invention is simple and inexpensive to produce.

BRIEF DESCRIPTION OF THE FIGURES

The invention will be described below with reference to preferred embodiments and to the attached drawings, in which.

DETAILED DESCRIPTION OF THE PREFERRED EMBODIMENTS

The present invention will now be described with reference to a preferred embodiment. As can be seen from FIG. 1, an embodiment of the absorbent article according to the invention is expediently a diaper 1 of the disposable type for infants. The diaper 1 comprises a first cover sheet constituting a liquid-permeable top sheet 2. This top sheet 2 is arranged on that side of the diaper 1 which, during use, is intended to be directed towards the person wearing the diaper. The diaper 1 further comprises a second cover sheet constituting a liquid-tight bottom sheet 3 which, during use, is intended to be directed away from the user, i.e., on the underside of the diaper. An absorption body 4 is arranged between the top sheet 2 and the bottom sheet 3. The absorption body 4 is preferably of a type known per se and is designed to rapidly take up liquid excretions on the surface of the diaper 1 and also to convey such excretions to a lower absorbent structure in the absorption body 4. As is already known per se, the absorption body 4 can, for example, comprise a soft wadding material which functions as a layer for conveying and distributing liquid excrement and urine which passes through the top sheet 2. Under this wadding material, the absorption body 4 can expediently comprise a highly absorbent material which optimally takes up and stores bodily excretions. In a possible variant, the absorption body 4 can include what is called a superabsorbent material, for an especially high degree of absorption of liquid. The design of the absorption body 4 can follow the known prior art and can include various materials, for example different synthetic and natural fibers, or fibre combinations, and the absorption body 4 can be defined by different material layers or by a single layer with good properties as regards taking up, spreading and storing bodily fluids.

Figure 1:
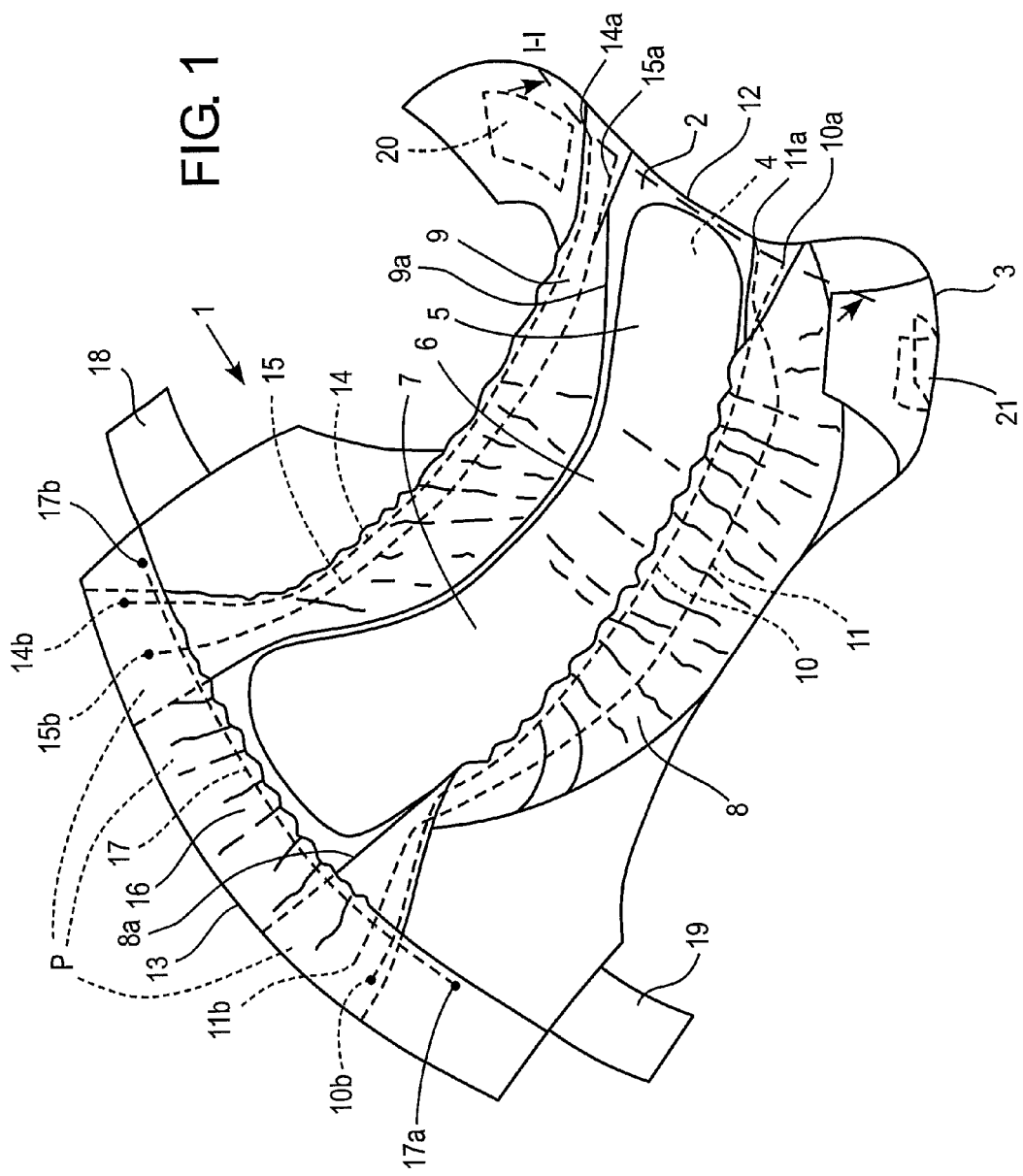
FIG. 1 shows a perspective view of an absorbent article in the form of a diaper, in which the present invention can be used.

The liquid-permeable top sheet 2 according to FIG. 1 preferably consists of a soft nonwoven material, but it can alternatively consist of other materials or material laminates. For example, it can consist of a perforated plastic film, for example of a thermoplastic material such as polyethylene or polypropylene, or a net-like layer of synthetic or textile material. Likewise, different types of laminates of suitable materials can be used as the liquid-permeable upper sheet. The nonwoven materials used are preferably nonwoven fibre layers of natural fibers, for example cellulose fibers or cotton fibers, or synthetic fibers such as polyethylene, polypropylene, polyester, nylon or the like. In addition, mixtures of different fibre types can be used for said nonwoven materials.

The top sheet 2 and the bottom sheet 3 can be joined together (the absorption body 4 being arranged between these layers) with the aid of a suitable joining method, for example adhesive bonding or ultrasonic welding.

Thus, a top sheet 2 made of nonwoven material is preferably used, but, irrespective of the material chosen, the top sheet 2 is intended in a manner known per se to receive and let through liquid excretions from the user and convey these downwards to the underlying absorption body 4. Leakage further through the absorption body 4 is prevented by the underlying liquid-impermeable bottom sheet 3, which is made of a liquid-impermeable material preferably in the form of a thin and liquid-tight plastic film. For example, plastic films made of polyethylene, polypropylene or polyester can be used. A material of the type which is breathable is preferably used for the bottom sheet 3. Moreover, a laminate comprising suitable material layers can be used as the liquid-tight bottom sheet 3.

As can be seen from FIG. 1, the diaper 1 has a basically elongated shape and is generally formed to fit around the lower trunk of an infant when in use. For this purpose, the diaper 1 is designed so that it defines, in its longitudinal direction, a front portion 5, a middle portion 6, and a rear portion 7. When the diaper 1 is in use, the front portion 5 is positioned so that it is directed towards the user's belly and down towards the groin area, while the crotch portion 6 is positioned basically directly below the user's crotch, and the rear portion 7 is positioned so that it is directed towards the user's buttocks. The boundaries between the abovementioned portions 5, 6, 7 do not need to be defined with exact dimensions and they do not occur at a specified transverse position for example, but instead along extended transition areas.

As regards the function, dimensions and design of the diaper 1, it is designed in particular to be used on very small infants, including premature babies, in other words babies born before the full term of pregnancy. For this reason, the diaper 1 is preferably designed with a special side barrier structure in order to prevent leakage of bodily excretions, in particular, in the form of loose and runny excrement, in the transverse direction of the diaper 1, i.e., sideways towards the user's legs. More specifically, the diaper 1 is therefore designed with two elongated and longitudinal side edges which form a first elastic side barrier 8 and a second elastic side barrier 9 along the respective side of the diaper 1. As will be described in detail below, these side barriers 8, 9 prevent leakage of urine and excrement out from the diaper 1 towards the user's legs.

The two side barriers 8, 9 are preferably made of a hydrophobic nonwoven material and extend upwards from the respective longitudinal edge of the absorption body 4 so that, when the diaper 1 is in use, they define elastic walls or barriers which bear against and provide a seal against the inside of the user's legs in order to prevent leakage of urine and excrement. In contrast to known diapers which normally comprise separate side barriers and leg elastic components, the two side barriers 8, 9 on their own constitute a combined side leakage protection and leg elastic.

The first side barrier 8 is provided with a first elastic element 10 and a second elastic element 11. The first elastic element 10 preferably consists of an elastic thread which is secured near the edge of the first side barrier 8 and runs between two attachment points 10a, 10b near the front edge 12 and near the rear edge 13, respectively, of the diaper 1. The second elastic element 11 also preferably consists of an elastic thread which extends between the first elastic element 10 and the bottom edge of the side barriers 8 and runs between two attachment points 11a, 11b near the front edge 12 and near the rear edge 13, respectively of the diaper 1. The two elastic elements 10, 11 are preferably attached at points along the first side barrier 8. However, the invention can also be realized without such attachment, i.e. such that the elastic elements 10, 11 can instead be allowed to run freely along the first side barrier 8.

Correspondingly, the second side barrier 9 is provided with a third elastic element 14 and a fourth elastic element 15. The third elastic element 14 preferably consists of an elastic thread which is arranged near the edge of the second side barrier 9 and runs between two attachment points 14a, 14b near the front edge 12 and near the rear edge 13, respectively, of the diaper 1. The fourth elastic element 15 also preferably consists of an elastic thread which extends between the third elastic element 14 and the bottom edge of the second side barrier 9 and runs between two attachment points 15a, 15b near the front edge 12 and near the rear edge 13, respectively, of the diaper 1. In a manner analogous to what has been described above, the third and fourth elastic elements 14, 15 are also preferably attached at points along the second side barrier 9, but alternatively they can also be allowed to run freely along the second side barrier 9. The attachments of the elastic elements 10, 11, 14, 15 are preferably made by adhesive bonding, alternatively by ultrasonic welding. Such attachment methods are already known per se and are therefore not described in detail here.

The two side barriers 8, 9 are secured to the top sheet 2 in a suitable manner, e.g., by ultrasonic welding or adhesive bonding. In this way, a first longitudinal fold, which is also a line of attachment, 8a is formed where the first side barrier 8 meets the top sheet 2, and a second longitudinal fold, which is also a line of attachment 9a, is formed where the second side barrier 9 meets the top sheet 2.

In addition to the diaper 1 being intended to provide safety against leakage in the lateral direction, an important aim of the two side barriers 8, 9 is to contribute to the diaper 1 enclosing the user's buttocks in a leaktight manner. This is preferably achieved by virtue of the fact that the side barriers 8, 9 cooperate with a further leakage protection at the waist opening at the rear of the diaper 1. Referring to FIG. 1, it will be seen that the diaper 1 according to the invention comprises a rear barrier 16 which runs transverse to the longitudinal direction of the diaper 1, in the area behind the rear portion 7 of the diaper 1. The aim of this rear barrier 16 is mainly to reduce the risk of leakage of loose excrement in the rearward direction, i.e., up towards the user's back. For this purpose, the rear barrier 16 is preferably provided with a fifth elastic element 17 which, like the abovementioned elastic elements 10, 11, 14, 15, preferably consists of an elastic thread running along the edge of the rear barrier 16 in such a way that it extends across all of the abovementioned elastic elements 10, 11, 14, 15. The fifth elastic element 17 ends at two attachment points 17a, 17b, in the manner shown in FIG. 1.

In this way, the rear barrier 16 defines a pocket P in the rear part of the diaper 1 and cooperates with the two side barriers 8, 9 in such a way that they together form an elastic barrier along the sides and rear part of the diaper 1. The diaper 1 is preferably designed so that the outer attachment points 17a, 17b for the fifth elastic element 17, viewed from above, are positioned outside the rear attachment points 10b, 14b of the outer elastic elements 10, 14.

It will further be seen from FIG. 1 that each side barrier 8, 9 is arranged in such a way that it is secured in contact with said front portion 5 of the diaper. More precisely, each side barrier 8, 9 is secured in such a way that each side barrier 8, 9 and the top sheet 2 define a structure of substantially Z-shaped cross section, i.e., the side barriers 8, 9 are folded in contact with the front edge such that the side barriers 8, 9 and the top sheet 2 define this Z-shaped form. This feature, which will be described in more detail with reference to FIG. 4, helps the diaper 1 open out easily when being used. The rear barrier 16 is also designed to enclose the user's buttocks in an advantageous way between the two side barriers 8, 9 which, at the rear of the diaper 1, are placed at a relatively great distance from each other. In addition, this design of the rear barrier 16 affords a secure seal against leakage of excrement and urine rearwards and over the rear edge of the diaper 1. A further advantage of this design is that the diaper 1 is very easy to fit on the user.

To make the diaper 1 easier to fit on the user, it is designed with two tape-like fastening strips 18, 19 which are arranged in the rear portion 7 of the diaper 1. The fastening strips 18, 19 are intended to cooperate and are secured in a releasable manner against corresponding fastening areas 20, 21 (which are indicated symbolically by broken lines) in the front portion 5 of the diaper 1. The fastening strips 18, 19 can be secured on the fastening areas 20, 21 by means of the fastening strips 18, 19 being provided with a suitable adhesive for example, or alternatively by their being designed as velcro-type fasteners or in some other suitable manner. As an alternative to the fastening areas 20, 21 shown in FIG. 1, the diaper 1 can be provided with a single fastening area which can then be located centrally on the front portion of the diaper. This contributes to an improved fit of the diaper 1.

In FIG. 1, the diaper 1 is shown as it appears during use. The figure shows that each side barrier 8, 9 is raised relatively high from the top sheet 2 of the diaper 1. It should also be noted that the diaper 1 does not comprise any separate leg elastic as in conventional diapers. The design affords advantages, especially in the form of limited material consumption, a better fit, and a reduced risk of leakage over the sides. The rear elastic barrier 16 also provides a greater possibility of taking up loose excrement in the rearward direction, i.e., towards the user's back.

The requirement relating to effective sealing and safety against leakage in the rearward direction over the opening defined at the waist is satisfied in particular by the rear elastic barrier 16 and its interaction with the two side barriers 8, 9. Since the distance between the two side barriers 8, 9 at the rear of the diaper 1 is relatively large, effective sealing is required at the waist opening in order to prevent leakage. This is achieved in particular by the fact that the rear barrier 16 comprises the abovementioned fifth elastic element 17 (expediently consisting of an elastic thread) which preferably extends at least as far as the outermost elastic elements of the side barriers 8, 9, i.e., the abovementioned first elastic element 10 and fourth elastic element 14. More precisely, attachment points for the fifth elastic element 17 are chosen which provide a continuous barrier along the longitudinal sides and the waist opening at the rear.

Figure 2:
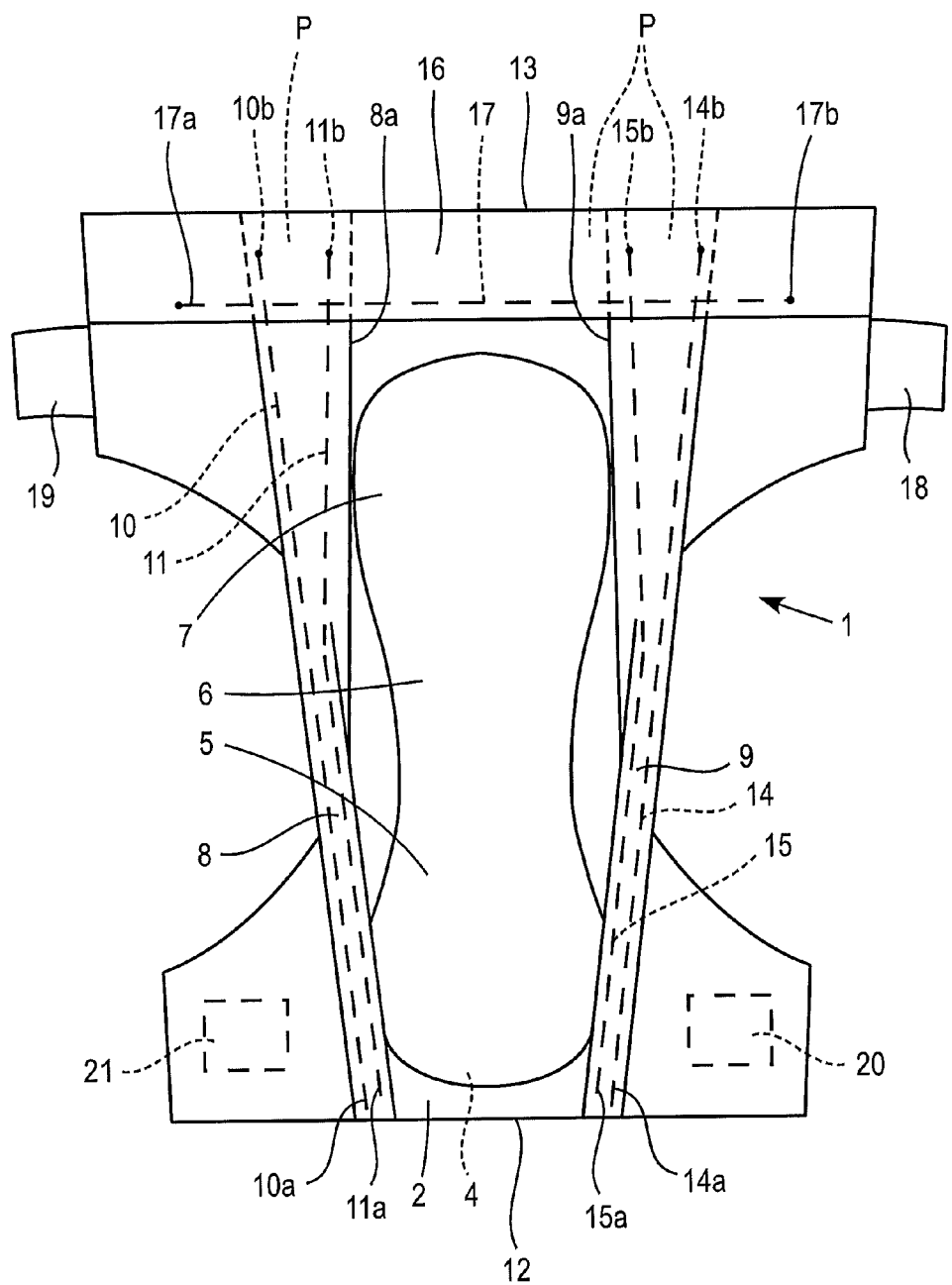
FIG. 2 shows a diagrammatic and somewhat simplified top view of the diaper according to FIG. 1.

As can be seen from FIG. 2, which is a diagrammatic top view of the diaper 1, another fundamental feature is that the distance between the rear attachment point 10b of the first elastic element 10 and the rear attachment point 14b of the third elastic element 14 is greater than the distance between the front attachment point 10a of the first elastic element 10 and the front attachment point 14a of the third elastic element 14. Correspondingly, the distance between the rear attachment point 11b of the second elastic element 11 and the rear attachment point 15b of the fourth elastic element 15 is greater than the distance between the front attachment point 11a of the second elastic element 11 and the front attachment point 15a of the fourth elastic element 15. This means that the four elastic elements 10, 11, 14, 15, viewed from above, run alongside each other in such a way that, together with the respective side barrier 8, 9, they form a narrowing structure, i.e., in the direction from the rear portion 7 of the diaper 1 towards its front portion 5. By virtue of the fact that the distance of the side barriers 8, 9 from each other is therefore less at the front than at the rear of the diaper 1, the latter is easy to fit on the user.

It should be noted in particular that the rear attachment point 10b of the first elastic element 10 lies outside the rear attachment point 11b of the second elastic element 11 (viewed in relation to an imaginary longitudinal axis of symmetry running along the longitudinal direction of the diaper 1). Likewise, the rear attachment point 14b of the third elastic element 14 lies outside the rear attachment point 15b of the fourth elastic element 15.

The attachment of the elastic elements 10, 11, 14, 15 in the front portion 5 of the diaper 1 is analogous to the attachment in the rear portion 7. Thus, the front attachment point 10a of the first elastic element 10 lies outside the front attachment point 11a of the second elastic element 11, while the front attachment point 14a of the third elastic element 14 lies outside the front attachment point 15a of the fourth elastic element 15. However, it should be noted that the actual material of the respective side barrier 8, 9 is folded like a V at the attachment to the front portion of the diaper 1, as has been described above.

As can be seen from FIGS. 1 and 2, the rear part of each side barrier 8, 9 is designed so that it forms an outwardly folded and essentially open, cup-shaped structure by virtue of the fact that the first elastic element 10 is attached to the rear of the diaper 1 at a point 10b which, viewed from above, lies outside the attachment point 11b for the second elastic element 11 and the first longitudinal fold, which is also a line of attachment 8a. Correspondingly, the attachment point 14b for the third elastic element 14 lies outside the attachment point 15b for the fourth elastic element 15 and outside the second longitudinal fold, which is also a line of attachment 9a. In this way, the side barriers 8, 9 will lift effectively and form a cup-like structure during use. This is facilitated by the fact that the respective side barrier 8, 9 additionally comprises two longitudinal elastic elements each (10, 11 and 14, 15, respectively). The narrowing geometry in the forward direction defined by the side barriers 8, 9 and the elastic elements 10, 11, 14, 15, and the Z-shaped attachment at the front, also contribute to stretching and lifting the side barriers 8, 9.

To ensure that the side barriers 8, 9 will enclose the user's buttocks and will not get in the way when placing the front part of the diaper 1 on the user, the distance between the rear attachment points 10b, 14b of the laterally outer elastic elements 10, 14 (outer edges of the barrier) should be at least twice as great, preferably at least three times as great, as the corresponding distance at the front, i.e., the distance between the front attachment point 10a of the first elastic element 10 and the front attachment point 14a of the third elastic element 14.

Moreover, the distance between the front attachment point 11a of the second elastic element 11 and the front attachment point 15a of the fourth elastic element 15 is preferably within the range of 1-3 cm. In this way, a space is created, at the front of the diaper 1, which can be considered sufficiently large for small infants, but which is not so wide as to prevent application of the diaper 1.

Figure 3:
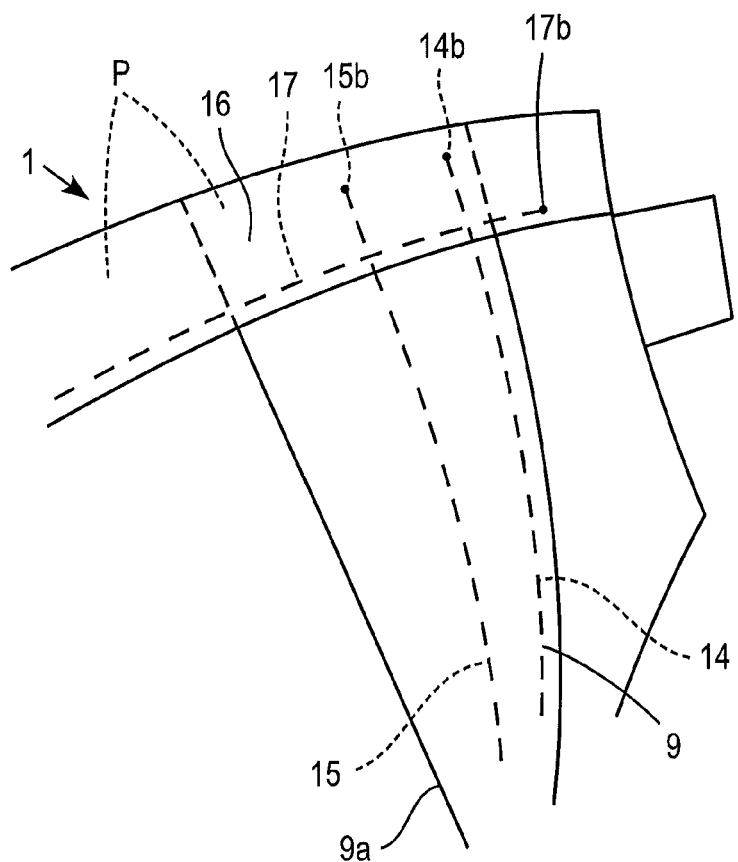
FIG. 3 shows a slightly enlarged perspective view of the rear part of the diaper according to FIGS. 1 and 2.

FIG. 3 shows a perspective view of the rear part of the diaper 1 according to FIGS. 1 and 2. More precisely, FIG. 3 shows in detail how the rear part of the second side barrier 9 is attached in the rear part of the diaper 1. This attachment allows the side barrier 9 to be folded out so that a cup-shaped structure is formed. This is achieved by the fact that the third elastic element 14 runs along the edge of the second side barrier 9 and onwards under the rear barrier 16 to its rear attachment point 14b. This rear attachment point 14b is thus situated inside the second side barrier 9, which in turn extends under the rear barrier 16. The fourth elastic element 15 also runs along the second side barrier 9 and onwards under the rear barrier 16 to its rear attachment point 15b. The second longitudinal fold, which is also a line of attachment, 9a then runs along the distance where the second side barrier 9 meets the top sheet 2 and ends under the rear barrier 16. The fifth elastic element 17 runs across the rear section of the second side barrier 16 so that a rear pocket is formed, the fifth elastic element 17 having one attachment point 17b outside the third elastic element 14 and the fourth elastic element 15 (viewed from above).

Figure 4:
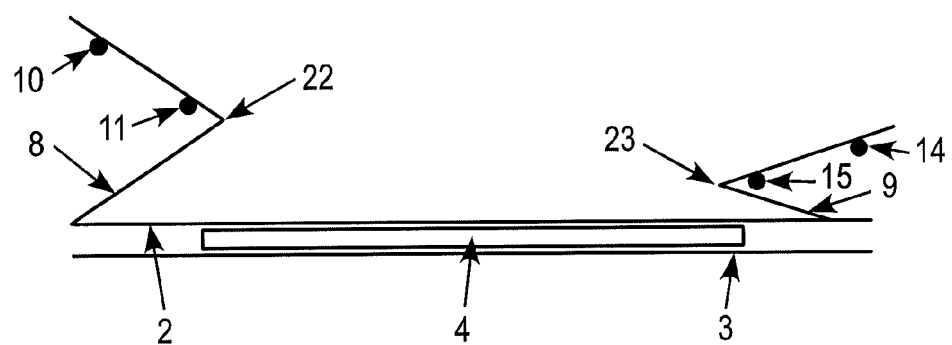
FIG. 4 shows a cross-sectional view of the side barriers, the elastic elements, the liquid-permeable cover sheet, the liquid-impermeable cover sheet, and the absorption body, the side barriers and the liquid-permeable cover sheet defining a folded structure of substantially Z-shaped cross section according to FIGS. 1-3.

The Z-shaped structure defined by the top sheet 2 and each side barrier 8, 9 can be seen clearly from FIG. 4, which is a somewhat simplified and diagrammatic view of a cross section through the diaper 1, viewed at the front edge of the diaper 1, as is indicated by the line I-1 in FIG. 1. The left-hand part of FIG. 4 shows an imaginary situation during production and shaping of the structure to give the Z-shaped configuration. The right-hand part of FIG. 4 shows the structure after it has been folded. FIG. 4 shows how the first side barrier 8 is folded and also supports the first elastic element 10 and the second elastic element 11. Correspondingly, the second side barrier 9 is folded and supports the third elastic element 14 and the fourth elastic element 15. Two folds 22, 23 are thus formed in the respective side barrier 8, 9, namely a first fold 22 in the first side barrier 8 and a second fold 23 in the second side barrier 9. These folds 22, 23 are directed towards the inside of the diaper 1, i.e., in the direction towards an imaginary longitudinal axis of symmetry of the diaper 1. The inner elastic elements 11, 15, i.e., the second elastic element 11 and the fourth elastic element 15, are thus positioned at or near the respective fold 22, 23 which is formed. The other elastic threads 10, 14 are then applied where suitable between the inner threads 11, 15 and the outermost edge of the respective side barrier 8, 9.

The side barriers 8, 9 are arranged such that their respective front portion and the top sheet 2 define a Z shape, the front part of the second elastic element 11 and the fourth elastic element 15 being positioned in contact with the inner folds 22, 23. The rear part of the respective side barrier 8, 9, however, defines no such Z shape but instead forms raised side walls which contribute to the cup-shaped and leaktight rear part 7 of the diaper 1. The fact that the side barriers 8, 9 are folded out in the rear portion 7 of the diaper 1 and define a Z shape with the front portion 5 of the diaper 1 ensures a good fit of the diaper 1. The diaper 1 is also made easy to place on a user and permits effective lifting of the side barriers 8, 9 during use of the diaper 1, a good fit and a high degree of protection against leaking.

Each side barrier 8, 9 is thus attached to the top sheet 2 with the Z-shaped configuration at the front end of the respective side barrier 8, 9 (see FIG. 1). The Z-shaped portion expediently extends from the front edge 12 of the diaper and at least as far as the front edge of the absorption body 4. However, the invention is not limited to this, and instead the Z-shaped portion can alternatively have another extent.

The invention is not limited to the embodiments described above and instead it can be varied within the scope of the attached claims. For example, different types of elastic elements can be used in the respective side barrier 8, 9, for example threads, bands, films, nonwoven material or the like. The number of elastic elements can also be varied, although, if they are in the form of threads, they must be at least two in number. If threads are used, two or more threads can be used in the side barriers 8, 9 so as to distribute the pressure of the elastic against the sensitive body of the child.

If, for example, a wide elastic is used, this should extend from the respective fold in the Z shape, in the same way as the innermost elastic thread must be applied at or near the fold (see FIG. 3).

Although this has not been described above, a diaper according to an alternative embodiment can have further elastic elements, preferably in the form of two coil-like portions, along the front end edge 12 and the rear end edge 13. These elastic elements can be formed to close against the user's stomach and back, respectively, by which means the diaper acquires the desired fit and comfort during use.

The diaper according to the invention can in principle be designed without the abovementioned rear barrier 16 with its elastic element 17. This design detail affords an advantage in terms of a reduced risk of leakage of loose excrement upwards over the rear edge 13 in the direction towards the user's back, but it should be noted the above-described advantages of the side barriers 8, 9 can be achieved irrespective of whether a rear barrier 16 is used.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent article defining a longitudinal direction, a front portion in the longitudinal direction, a rear portion, and a middle portion arranged between said front and rear portions, the article comprising:
   an upper, liquid-permeable cover sheet,
   a lower, liquid-impermeable cover sheet,
   an absorption body arranged between the cover sheets,
   a rear barrier formed in the rear portion and attached to the article along a rear edge of the article, and
   first and second side barriers along respective longitudinal sides, each side barrier in turn comprising at least one longitudinal elastic element, said first and second side barriers, viewed from above, defining a shape which narrows in the direction towards said front portion so that the distance, in the transverse direction of the article, between said elastic elements, is greater in said rear portion than in said front portion,
   each side barrier is arranged such that each side barrier is secured in contact with said front portion, and each side barrier and the upper cover sheet define a folded structure of substantially Z-shaped cross section with a fold directed towards the inside of said article, wherein the at least one longitudinal elastic element of each side barrier is positioned at or near the fold directed towards the inside of the article, the at least one longitudinal elastic element of each side barrier runs between an attachment point on the front portion of the article and an attachment point on the rear portion of the article and along the entire length of the fold directed towards the inside of the article, and the first side barrier is secured to the upper cover sheet to form a first line of attachment, and the second side barrier is secured to the upper cover sheet to form a second line of attachment, the first and second lines of attachment extending under the rear barrier, and the first and second side barriers cooperate with the rear barrier to form a pocket, the pocket extending to the rear edge of the article and continuously between and beyond the first and second lines of attachment in respective outward transverse directions of the article.

2. The absorbent article according to claim 1, wherein the elastic element in the first side barrier, viewed from above, is secured to said rear portion outside the first line of attachment, and the elastic element in the second side barrier, viewed from above, is secured to said rear portion outside the second line of attachment.

3. The absorbent article according to claim 1, wherein the rear barrier is intended for taking up bodily excretions in the direction rearwards along said article.

4. The absorbent article according to claim 1, wherein said rear barrier comprises a further elastic element.

5. The absorbent article according to claim 4, wherein said further elastic element, when viewed from above, extends outside the attachment points on the rear portion of the article, and wherein said further elastic element comprises attachment points which, when viewed from above, extend outside the attachment points of the elastic elements in the side barriers on the rear portion of the article, a barrier being defined along the longitudinal sides and rear side of said article.

6. The absorbent article according to claim 1, wherein said first side barrier comprises a first elastic element and a second elastic element, said second side barrier comprises a third elastic element and a fourth elastic element, said first elastic element extending outside the second elastic element viewed in relation to a longitudinal axis of symmetry through said article, and said third elastic element extending outside the fourth elastic element viewed in relation to said axis of symmetry.

7. The absorbent article according to claim 1, wherein the distance between the elastic elements of the side barriers is at least two times greater at said rear portion than at said front portion.

8. The absorbent article according to claim 1, wherein the distance between the elastic elements of the side barriers is at least three times greater at said rear portion than at said front portion.

9. The absorbent article according to claim 1, wherein the distance between parts of the elastic elements in the side barriers nearest to the inside of said article is within the range of 1-3 cm at said front portion.

10. The absorbent article according to claim 1, wherein the elastic elements run at least partially in contact with said folds in each side barrier.

11. The absorbent article according to claim 1, wherein the said first and second side barriers by themselves constitute a combined side leakage protection and leg elastic for said article.

12. The absorbent article according to claim 1, wherein the said elastic elements consist of elastic threads.

13. The absorbent article according to claim 1, wherein the entire pocket is provided beyond the absorption body in the longitudinal direction.

14. The absorbent article according to claim 1, wherein the first and second side barriers form a side barrier of the pocket in the longitudinal direction of the article, the side barrier of the pocket being disposed beyond the first and second lines of attachment in the transverse direction of the article.

15. The absorbent article according to claim 1, wherein the at least one longitudinal elastic element of each side barrier is positioned at or near the fold along an entire length of the at least one longitudinal elastic element.

16. An absorbent article defining a longitudinal direction, a front portion in the longitudinal direction, a rear portion, and a middle portion arranged between said front and rear portions, the article comprising:

an upper, liquid-permeable cover sheet,
a lower, liquid-impermeable cover sheet,
an absorption body arranged between the cover sheets, and
first and second side barriers along respective longitudinal sides, each side barrier in turn comprising at least one longitudinal elastic element, said first and second side barriers, viewed from above, defining a shape which narrows in the direction towards said front portion so that the distance, in the transverse direction of the article, between said elastic elements, is greater in said rear portion than in said front portion, each side barrier is arranged such that each side barrier is secured in contact with said front portion, and each side barrier and the upper cover sheet define a folded structure of substantially Z-shaped cross section with a fold directed towards the inside of said article, wherein the at least one longitudinal elastic element of each side barrier is positioned at or near the fold directed towards the inside of the article, the at least one longitudinal elastic element of each side barrier runs between an attachment point on the front portion of the article and an attachment point on the rear portion of the article and along the entire length of the fold directed towards the inside of the article;

the article further comprising a rear barrier formed in said rear portion and attached to the article along the rear edge of the article, which rear barrier is intended for taking up bodily excretions in the direction rearwards along said article, the first side barrier is secured to the upper cover sheet to form a first line of attachment, and the second side barrier is secured to the upper cover sheet to form a second line of attachment, the first and second lines of attachment extending under the rear barrier, and the first and second side barriers cooperate with the rear barrier to form a pocket, the pocket extending to the rear edge of the article and continuously between and beyond the first and second lines of attachment in respective outward transverse directions of the article, said rear barrier comprises a further elastic element,
said further elastic element, when viewed from above, extends outside the attachment points on the rear portion of the article, and
said further elastic element comprises attachment points which, when viewed from above, extend outside said attachment points of the elastic elements in the side barriers on the rear portion of the article, a barrier being defined along the longitudinal sides and rear side of said article.

17. The absorbent article according to claim 16, wherein the entire pocket is provided beyond the absorption body in the longitudinal direction.

18. The absorbent article according to claim 16, wherein the first and second side barriers form a side barrier of the pocket in the longitudinal direction of the article, the side barrier of the pocket being disposed beyond the first and second lines of attachment in the transverse direction of the article.

19. The absorbent article according to claim 16, wherein the at least one longitudinal elastic element of each side barrier is positioned at or near the fold along an entire length of the at least one longitudinal elastic element.

* * * * *